United States Patent [19]

Elbe et al.

[11] Patent Number: 5,081,265

[45] Date of Patent: Jan. 14, 1992

[54] MICROBICIDAL SUBSTITUTED DIOXOLANES

[75] Inventors: Hans-Ludwig Elbe; Eckart Kranz, both of Wuppertal; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 582,581

[22] Filed: Sep. 14, 1990

Related U.S. Application Data

[62] Division of Ser. No. 389,032, Aug. 3, 1989, Pat. No. 4,988,715.

[30] Foreign Application Priority Data

Aug. 10, 1988 [DE] Fed. Rep. of Germany ....... 3827134

[51] Int. Cl.$^5$ .......................................... C07D 317/14
[52] U.S. Cl. .................................................. 549/448
[58] Field of Search ......................... 549/448; 514/467

[56] References Cited

U.S. PATENT DOCUMENTS

| | | | |
|---|---|---|---|
| 4,417,050 | 11/1983 | Cherpeck | 544/335 |
| 4,549,900 | 10/1985 | Kramer et al. | 71/92 |
| 4,639,462 | 1/1987 | Krämer et al. | 514/383 |

FOREIGN PATENT DOCUMENTS

0046532 3/1982 European Pat. Off. .

OTHER PUBLICATIONS

Chemical Abstracts, vol. 87, Jul. 4, 1977, No. 1, 6280j.
Chemical Abstracts, vol. 70, Mar. 31, 1969, No. 13, 58196e.
Chemical Abstracts, vol. 96, Apr. 26, 1982, No. 17, 141929d.
Chemical Abstracts, vol. 102, Mar. 4, 1985, No. 9, 77968d.
Chemical Abstracts, vol. 106, May 25, 1987, No. 21, 176799p.
Chemical Abstracts, vol. 109, Aug. 1, 1988, No. 5, 38060b.
Chemical Abstracts, vol. 101, Nov. 19, 1984, No. 21, 191762m.
Chemical Abstracts, vol. 103, Sep. 30, 1985, No. 13, 104770n.

*Primary Examiner*—C. Warren Ivy
*Assistant Examiner*—Ba K. Trinh
*Attorney, Agent, or Firm*—Sprung, Horn, Kramer & Woods

[57] ABSTRACT

Fungicidal dioxolanes of the formula (I)

in which
$R^1$ represents optionally substituted alkyl, optionally substituted alkenyl, optionally substituted alkinyl, optionally substituted cycloalkyl, optionally substituted cycloalkylalkyl, optionally substituted aryl, optionally substituted aryloxy, optionally substituted arylthio, optionally substituted arylsulphinyl, optionally substituted arylsulphonyl, optionally substituted arylalkyl, optionally substituted aryloxyalkyl, optionally substituted arylthioalkyl, optionally substituted arylsulphinylalkyl, optionally substituted arylsulphonylalkyl, optionally substituted aralkyloxyalkyl, optionally substituted aralkylthioalkyl, optionally substituted aralkylsulphinylalkyl or optionally substituted aralkylsulphonylalkyl.
$R^2$, $R^3$, $R^4$, $R^5$ and $R^6$ independently of one another represent hydrogen, alkyl or cycloalkyl, or
$R^3$ and $R^4$ together represent divalent alkanediyl and/or $R^5$ and $R^6$ together represent divalent alkanediyl and
A represents nitrogen or a CH group, and addition products thereof with acids and metal salts. Also novel intermediates of the formulas (IIa), (VIIa), (Va) and (XIIa).

1 Claim, No Drawings

MICROBICIDAL SUBSTITUTED DIOXOLANES

This is a division of application Ser. No. 389,032, filed Aug. 3, 1989, now U.S. Pat. No. 4,988,785.

The invention relates to new substituted dioxolanes, a process for their preparation and their use as microbicides.

It is known that certain carbinols having heterocyclic substituents possess fungicidal properties (compare EP-OS 0,055,833 and U.S. Pat. No. 4,417,050). Thus, for example, 4-(4-chlorophenyl)-3,3-dimethyl-1-(1,2,4-triazol-1-yl)-2-butanol and (4-chlorophenyl)-(5-pyrimidinyl)-methanol can be used for combating fungi. However, the activity of these substances is not always completely satisfactory, especially when low amounts are applied.

New substituted dioxolanes of the formula

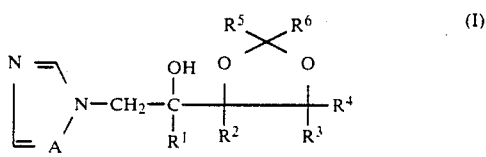

in which

R$^1$ represents optionally substituted alkyl, optionally substituted alkenyl, optionally substituted alkinyl, optionally substituted cycloalkyl, optionally substituted cycloalkylalkyl, optionally substituted aryl, optionally substituted arylalkyl, optionally substituted aryloxyalkyl, optionally substituted arylthioalkyl, optionally substituted arylsulphinylalkyl, optionally substituted arylsulphonylalkyl, optionally substituted aralkyloxyalkyl, optionally substituted aralkylthioalkyl, optionally substituted aralkylsulphinylalkyl, or optionally substituted aralkylsulphonylalkyl, R$^2$, R$^3$, R$^4$, R$^5$ and R$^6$ independently of one another represent hydrogen, alkyl or cycloalkyl, or R$^3$ and R$^4$ together represent divalent alkanediyl and/or R$^5$ and R$^6$ together represent divalent alkanediyl and A represents nitrogen or a CH group, and acid addition salts and metal salt complexes thereof, have now been found.

The substances of the formula (I) according to the invention possess two or more asymmetrically substituted carbon atoms, depending on the nature of the substituents R$^1$ to R$^6$, and can therefore occur in the form of optical isomers or diastereomers. The invention relates both to pure isomers and to mixtures thereof of varying composition.

It has furthermore been found that substituted dioxolanes of the formula (I) and acid addition salts and metal salt complexes thereof are obtained by a process in which oxiranyl-dioxolanes of the formula

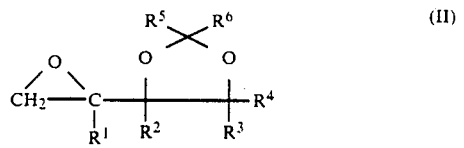

in which

R$^1$, R$^2$, R$^3$, R$^4$, R$^5$ and R$^6$ have the abovementioned meanings, are reacted with azoles of the formula

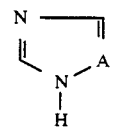

in which A has the abovementioned meaning, if appropriate in the presence of a diluent and if appropriate in the presence of a reaction auxiliary, and, if appropriate, an acid or a metal salt is then added on.

Finally, it has been found that the new substituted dioxolanes of the formula (I) and acid addition salts and metal salt complexes thereof have very good fungicidal properties.

Surprisingly, the substituted dioxolanes of the formula (I) according to the invention exhibit a considerably better fungicidal activity than 4-(4-chlorophenyl)-3,3-dimethyl-1-(1,2,4-triazol-1-yl)-2-butanol and (4-chlorophenyl)-(5-pyrimidinyl)-methanol, which are already known substances which are similar from the point of view of structure and action.

Formula (I) provides a general definition of the substituted dioxolanes according to the invention.

Unless defined otherwise, alkyl below in individual radicals and in radicals containing alkyl are, for example, straight-chain or branched alkyl having 1 to 12, preferably 1 to 8, in particular 1 to 7 and above all 3 to 7 carbon atoms.

Unless defined otherwise, alkenyl and alkinyl below is, for example, straight-chain or branched alkenyl or alkinyl having 2 to 12, preferably 2 to 8, in particular 2 to 7 and above all 3 to 7 carbon atoms.

Cycloalkyl in general contains 3 to 7, preferably 3 to 6, carbon atoms in the cycloalkyl part.

Aryl in general contains 6 to 10 carbon atoms in the aryl part, phenyl, α-naphthyl and β-naphthyl radicals being mentioned as examples.

These radicals can be substituted, for example, by one or more identical or different substituents from the following groups:

Halogen atoms, such as fluorine, chlorine, bromine and iodine, preferably fluorine, chlorine and bromine, cyano, nitro, in each case straight-chain or branched alkyl, alkoxy, alkylthio, alkylsulphinyl and alkylsulphonyl having in each case 1 to 8, preferably 1 to 6 and in particular 1 to 4 carbon atoms in the alkyl part, in each case straight-chain or branched halogenoalkyl, halogenoalkoxy, halogenoalkylthio, halogenoalkylsulphinyl and halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl parts, divalent dioxyalkylene which is unsubstituted or substituted by one or more identical or different halogen atoms, cycloalkyl having 3 to 7 carbon atoms and phenyl or phenoxy which is unsubstituted or substituted by one or more identical or different substituents from the group comprising halogen and/or straight-chain or branched alkyl having 1 to 4 carbon atoms.

Preferred compounds of the formula (I) are those in which

R$^1$ represents straight-chain or branched alkyl having 1 to 12 carbon atoms, straight-chain or branched alkenyl having 2 to 12 carbon atoms, straight-chain or branched alkinyl having 2 to 12 carbon atoms, alkoxyalkyl having 1 to 8 carbon atoms in the alkoxy part and 1 to 8 carbon atoms in the alkyl part, alkylthioalkyl having 1 to 8 carbon atoms in the alkylthio part and 1 to 8 carbon atoms in the alkyl part, alkylsulphinylalkyl having 1 to 8 carbon atoms in the alkylsulphinyl part and 1 to 8 carbon atoms in the alkyl part, alkylsulphonylalkyl having 1 to 8 carbon atoms in the alkylsulphonyl part and 1 to 8 carbon atoms in the alkyl part, alkoximinoalkyl having 1 to 8 carbon atoms in the alkoxy part and 1 to 8 carbon atoms in the alkyl part, hydroximinoalkyl having 1 to 8 carbon atoms, cyanoalkyl having 1 to 8 carbon atoms in the alkyl part, halogenoalkyl having 1 to 8 carbon atoms and 1 to 9 identical or different halogen atoms, halogenoalkoxyalkyl having 1 to 8 carbon atoms in the alkoxy part and 1 to 8 carbon atoms in the alkyl part and having 1 to 9 identical or different halogen atoms, halogenoalkylthioalkyl having 1 to 8 carbon atoms in the alkylthio part and 1 to 8 carbon atoms in the alkyl part and having 1 to 9 identical or different halogen atoms, halogenoalkylsulphinylalkyl having 1 to 8 carbon atoms in the halogenoalkyl part and 1 to 8 carbon atoms in the alkyl part and having 1 to 9 identical or different halogen atoms or halogenoalkylsulphonylalkyl having 1 to 8 carbon atoms in the halogenoalkyl part and 1 to 8 carbon atoms in the alkyl part and 1 to 9 identical or different halogen atoms, or represents halogenoalkenyl having 2 to 12 carbon atoms and 1 to 9 identical or different halogen atoms or halogenoalkinyl having 2 to 12 carbon atoms and 1 to 9 identical or different halogen atoms, or represents dioxolanylalkyl having 1 to 6 carbon atoms in the alkyl part, dithiolanylalkyl having 1 to 6 carbon atoms in the alkyl part or dioxanylalkyl having 1 to 6 carbon atoms in the alkyl part, or represents dithianylalkyl having 1 to 6 carbon atoms in the alkyl part, or $R^1$ represents cycloalkyl having 3 to 7 carbon atoms, it being possible for each of these cycloalkyl radicals to be substituted by one or more identical or different substituents from the group comprising halogen and/or alkyl having 1 to 4 carbon atoms, or $R^1$ represents cycloalkylalkyl having 3 to 7 carbon atoms in the cycloalkyl part and 1 to 8 carbon atoms in the alkyl part, it being possible for each of these radicals to be substituted in the cycloalkyl part by one or more identical or different substituents from the group comprising halogen and/or alkyl having 1 to 4 carbon atoms, or $R^1$ represents alkyl having 6 to 10 carbon atoms, arylalkyl having 6 to 10 carbon atoms in the aryl part and 1 to 8 carbon atoms in the alkyl part, aryloxyalkyl having 6 to 10 carbon atoms in the aryl part and 1 to 8 carbon atoms in the alkyl part, arylthioalkyl having 6 to 10 carbon atoms in the aryl part and 1 to 8 carbon atoms in the alkyl part, arylsulphinylalkyl having 6 to 10 carbon atoms in the aryl part and 1 to 8 carbon atoms in the alkyl part, arylsulphonylalkyl having 6 to 10 carbon atoms in the aryl part and 1 to 8 carbon atoms in the alkyl part, aralkyloxyalkyl having 6 to 10 carbon atoms in the aryl part and 1 to 8 carbon atoms in each alkyl part, aralkylthioalkyl having 6 to 10 carbon atoms in the aryl part and 1 to 8 carbon atoms in each alkyl part or aralkylsulphonylalkyl having 6 to 10 carbon atoms in the aryl part and 1 to 8 carbon atoms in each alkyl part, or represents aralkylsulphonylalkyl having 6 to 10 carbon atoms in the aryl part and 1 to 8 carbon atoms in each alkyl part, it being possible for each of the above-mentioned aryl radicals to be substituted in the aryl part by one or more identical or different substituents from the group comprising halogen, cyano, nitro, straight-chain or branched alkyl, straight-chain or branched alkoxy, straight-chain or branched alkylthio, straight-chain or branched alkylsulphinyl or straight-chain or branched alkylsulphonyl having in each case 1 to 4 carbon atoms, straight-chain or branched halogenoalkyl, straight-chain or branched halogenoalkoxy, straight-chain or branched halogenoalkylthio, straight-chain or branched halogenoalkylsulphinyl or straight-chain or branched halogenoalkylsulphonyl having in each case 1 to 4 carbon atoms and 1 to 9 identical or different halogen atoms, straight-chain or branched alkoxycarbonyl or straight-chain or branched alkoximinoalkyl having in each case 1 to 4 carbon atoms in the individual alkyl parts, divalent dioxyalkylene which is unsubstituted or substituted by one or more identical or different halogen atoms, cycloalkyl having 3 to 7 carbon atoms and phenyl or phenoxy which is unsubstituted or substituted by one or more identical or different substituents from the group comprising halogen and/or straight-chain or branched alkyl having 1 to 4 carbon atoms, $R^2$, $R^3$, $R^4$, $R^5$ and $R^6$ independently of one another each represent hydrogen, or represent straight-chain or branched alkyl having 1 to 6 carbon atoms, or represent cycloalkyl having 3 to 7 carbon atoms, it also being possible for either $R^3$ and $R^4$ together or $R^5$ and $R^6$ together to represent an alkanediyl radical, in each case divalent, having 2 to 6 carbon atoms, and A represents nitrogen or a CH group.

Particularly preferred compounds of the formula (I) are those in which $R^1$ represents in each case straight-chain or branched alkyl having 1 to 8 carbon atoms, alkenyl having 2 to 8 carbon atoms or alkinyl having 2 to 8 carbon atoms, or represents straight-chain or branched alkoxyalkyl, straight-chain or branched alkylthioalkyl, straight-chain or branched alkylsulphinylalkyl, straight-chain or branched alkylsulphonylalkyl, straight-chain or branched alkoximinoalkyl, straight-chain or branched hydroximinoalkyl or straight-chain or branched cyanoalkyl having in each case 1 to 6 carbon atoms in the individual alkyl parts, or represents straight-chain or branched halogenoalkyl, straight-chain or branched halogenoalkoxyalkyl, straight-chain or branched halogenoalkylthioalkyl, straight-chain or branched halogenoalkylsulphinylalkyl or straight-chain or branched halogenoalkylsulphonylalkyl having in each case 1 to 4 carbon atoms in the individual alkyl parts and in each case 1 to 5 identical or different halogen atoms, or represents straight-chain or branched halogenoalkenyl or straight-chain or branched halogenoalkinyl having in each case 3 to 8 carbon atoms and in each case 1 to 5 identical or different halogen atoms, or represents dioxolanylalkyl, dithiolanylalkyl, dioxanylalkyl or dithianylalkyl having in each case 1 to 4 carbon atoms in the straight-chain or branched alkyl part, or represents cycloalkylalkyl or cycloalkyl having in each case 3 to 6 carbon atoms in the cycloalkyl part and 1 to 6 carbon atoms in the straight-chain or branched alkyl part and in each case unsubstituted or substituted in the cycloalkyl part by 1 to 5 identical or different substituents, possible substituents in the cycloalkyl part in each case being: fluorine, chlorine and bromine and straight-chain or branched alkyl having 1 to 4 carbon atoms; or represents arylalkyl, aryloxyalkyl, arylthioalkyl, arylsulphinylalkyl, arylsulphonylalkyl, arylkyloxyalkyl, arylkylthioalkyl, aralkylsulphinylalkyl, arylkysulphonylalky or aryl having in each case 1 to 6 carbon atoms in the individual straight-chain or branched alkyl parts and in each case unsubstituted or substituted in the aryl part by 1 to 5 identical or different substituents, aryl in each case representing phenyl, α-naphthyl or β-naphthyl and possible substituents on the phenyl in each case being: fluorine, chlorine, bromine, cyano, nitro, methyl, ethyl, n- or i-propyl, n-, i-, s- or t-butyl, methoxy, ethoxy, n- or i-propoxy, methylthio, ethyl-thio, propane-1,3-diyl, butane-1,4-diyl, pentane-1,5-diyl, dimethylpropane-1,3-diyl, tetramethyl-propane-1,3-diyl, dimethylbutane-1,4-diyl, tetramethylbutane-1,4-diyl, cyclopropyl, cyclobutyl, cyclopentyl, cyclohexyl, trifluoromethyl, dichloro-fluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichlormethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromoethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene and dioxyethylene and phenyl or phenoxy, in each case unsubstituted or substituted by one to three identical or different substituents from the group comprising methyl, fluorine and chlorine; and possible substituents on the naphthyl in each case being: fluorine, chlorine, bromine, cyano, methyl, ethyl and n- or i-propyl, $R^2$, $R^3$, $R^4$, $R^5$ and $R^6$ independently of one another each represent hydrogen, methyl, ethyl, n- or i-propyl or n-, i-, s- or t-butyl, or represent cyclopentyl, or represent cyclohexyl, it also being possible for either $R^3$ and $R^4$ together or $R^5$ and $R^6$ together to represent a butane-1,4-diyl or pentane-1,5-diyl radical, which is in each case divalent, and A represents nitrogen or a CH group.

Especially preferred compounds of the formula (I) are those in which $R^1$ represents straight-chain or branched alkyl having 1 to 7 carbon atoms, straight-chain or branched alkenyl having 2 to 7 carbon atoms or straight-chain or branched alkinyl having 2 to 7 carbon atoms, or represents straight-chain or branched methoxyalkyl, straight-chain or branched dimethoxyalkyl, straight-chain or branched trimethoxyalkyl, straight-chain or branched methylthioalkyl, straight-chain or branched dimethylthioalkyl, straight-chain or branched trimethylthioalkyl, straight-chain or branched methylsulphinylalkyl, straight-chain or branched methylsulphonylalkyl, straight-chain or branched methoximinoalkyl, straight-chain or branched hydroximinoalkyl or straight-chain or branched cyanoalkyl having in each case 3 to 6 carbon atoms in the alkyl part, or represents straight-chain or branched halogenoalkyl, straight-chain or branched halogenomethoxyalkyl, straight-chain or branched halogenoethoxyalkyl, in each case straight-chain or branched halogenomethylthioalkyl or halogenomethylsulphinylalkyl or straight-chain or branched halogenomethylsulphonylalkyl having in each case 1 to 3 identical or different halogen atoms, in particular fluorine, chlorine or bromine, and having in each case 3 to 7 carbon atoms in the alkyl part, or represents straight-chain or branched halogenoalkenyl or straight-chain or branched halogenoalkinyl having in each case 3 to 7 carbon atoms and in each case 1 to 3 identical or different halogen atoms, in particular fluorine, chlorine or bromine, or represents dioxolanylalkyl, dithiolanylalkyl, dioxanylalkyl or dithianylalkyl having in each case 1 to 3 carbon atoms in the straight-chain or branched alkyl part; or represents cycloalkyl or cycloalkylalkyl having in each case 3 to 6 carbon atoms in the cycloalkyl part and 1 to 4 carbon atoms in the straight-chain or branched alkyl part and in each case unsubstituted or substituted in the cycloalkyl part by one to five identical or different substituents from the group comprising fluorine, chlorine, bromine and methyl; or represents phenyl, α-naphthyl or β-naphthyl, in each case unsubstituted or substituted by one to three identical or different substituents, or represents a radical of the formula

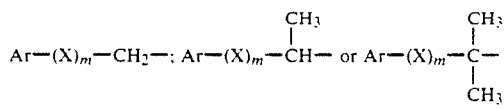

wherein

Ar in each case represents phenyl, α-naphthyl or β-naphthyl which is unsubstituted or substituted by one to three identical or different substituents, X represents oxygen, sulphur, sulphinyl or sulphonyl, or represents one of the groups —CH$_2$—; —O—CH$_2$—; —CH$_2$—O—; —O—CH$_2$—CH$_2$—; —S(O)$_n$—CH$_2$—; —CH$_2$—S(O)$_n$— or —S(O)$_n$—CH$_2$—CH$_2$—, m in each case represents the number 0 or 1 and n in each case represents the number 0, 1 or 2, possible substituents on the phenyl in each case being: fluorine, chlorine, bromine, cyano, nitro, methyl, ethyl, n- or i-propyl, n-, i-, s- or t-butyl, methoxy, ethoxy, n- or i-propoxy, methylthio, ethylthio, propane-1,3-diyl, butane-1,4-diyl, pentane-1,5-diyl, dimethylpropane-1,3-diyl, tetramethylpropane-1,3-diyl, dimethylbutane-1,4-diyl, tetramethylbutane-1,4-diyl, cyclopropyl, cyclobutyl, cyclopentyl, cyclohexyl, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorochloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene and dioxyethylene and phenyl and phenoxy which is unsubstituted or substituted by one to three substituents from the group comprising fluorine and chlorine; and possible substituents on the naphthyl in each case being: fluorine, chlorine, bromine, cyano, methyl, ethyl and n- or i-propyl, $R^2$, $R^3$, $R^4$, $R^5$ and $R^6$ independently of one another represent hydrogen or methyl and A represents nitrogen or a CH group.

Compounds of the formula (I) which are preferred in particular are those in which $R^1$ represents straight-chain or branched alkyl having 3 to 7 carbon atoms, straight-chain or branched alkenyl having 3 to 7 carbon atoms or straight-chain or branched alkinyl having 3 to 7 carbon atoms; or represents i-propyl or t-butyl, in each case substituted by one to three substituents from the group comprising fluorine, chlorine, methoxy, ethoxy, methylthio, ethylthio, trifluoromethyl, trifluoromethoxy and trifluoromethylthio; or represents methyl, ethyl, i-propyl or t-butyl, in each case monosubstituted by cyano, hydroximino, methoximino, ethoximino, cyclopentyl, cyclohexyl, dioxolanyl, dithiolanyl, dioxanyl or dithianyl; or represents in each case straight-chain or branched alkenyl or alkinyl having in each case 3 to 7 carbon atoms and substituted by one or two substituents from the group comprising fluorine, chlorine and bromine; or represents cyclopropyl, cyclobutyl, cyclopentyl, or cyclohexyl, in each case unsubstituted or substituted by one to five identical or different substituents from the group comprising fluorine, chlorine, bromine and methyl; or represents α-naphthyl or β-naphthyl; or represents phenyl which is unsubstituted or substituted by one to three identical or different substituents from the group comprising fluorine, chlorine, bromine, methyl, methoxy, methylthio, trifluoromethyl, trifluoromethoxy, trifluoromethylthio, difluoromethyl, difluoromethoxy, difluoromethylthio, phenyl and phenoxy; or represents a radical of the formula

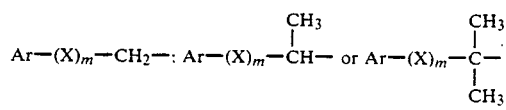

wherein

Ar in each case represents phenyl which is unsubstituted or substituted by one to three identical or different substituents from the group comprising fluorine, chlorine, bromine, methyl, methoxy, methylthio, trifluoromethyl, trifluoromethoxy, trifluoromethylthio, difluoromethyl, difluoromethoxy, difluoromethylthio, phenyl or phenoxy, or represents α-naphthyl or β-naphthyl which is in each case unsubstituted or substituted by fluorine, chlorine or methyl, X represents oxygen or sulphur, or represents one of the groups —$CH_2$—, —O—$CH_2$—, —S—$CH_2$—, —O—$CH_2$—$CH_2$— or —S—$CH_2$—$CH_2$— and m represents the number 0 or 1, $R^2$, $R^3$, $R^4$, $R^5$ and $R^6$ represents hydrogen and A represents nitrogen or a CH group.

Addition products of acids and those substituted dioxolanes of the formula (I) in which the substituents $R^1$, $R^2$, $R^3$, $R^4$, $R^5$, $R^6$ and A have the meanings which have already been mentioned as preferred for these substituents, in particular the acid addition products which are tolerated by plants, are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid, and saccharin or thiosaccharin.

Addition products of salts of metals of main group II to IV and sub-group I and II and IV to VIII and those substituted dioxolanes of the formula (I) in which the substituents $R^1$, $R^2$, $R^3$, $R^4$, $R^5$, $R^6$ and A have the meanings which have already been mentioned as preferred for these substituents, in particular the metal complexes which are tolerated by plants, are also preferred compounds according to the invention.

Salts of copper, zinc, manganese, magnesium, tin, iron and nickel are particularly preferred here. Possible anions of these salts are those which are derived from those acids which lead to addition products which are tolerated by plants. Particularly preferred acids of this type are in this connection the hydrogen halide acids, such as, for example, hydrochloric acid and hydrobromic acid, and nitric acid and sulphuric acid.

The following substituted dioxolanes of the general formula (I) may be mentioned specifically in addition to the compounds mentioned in the preparation examples:

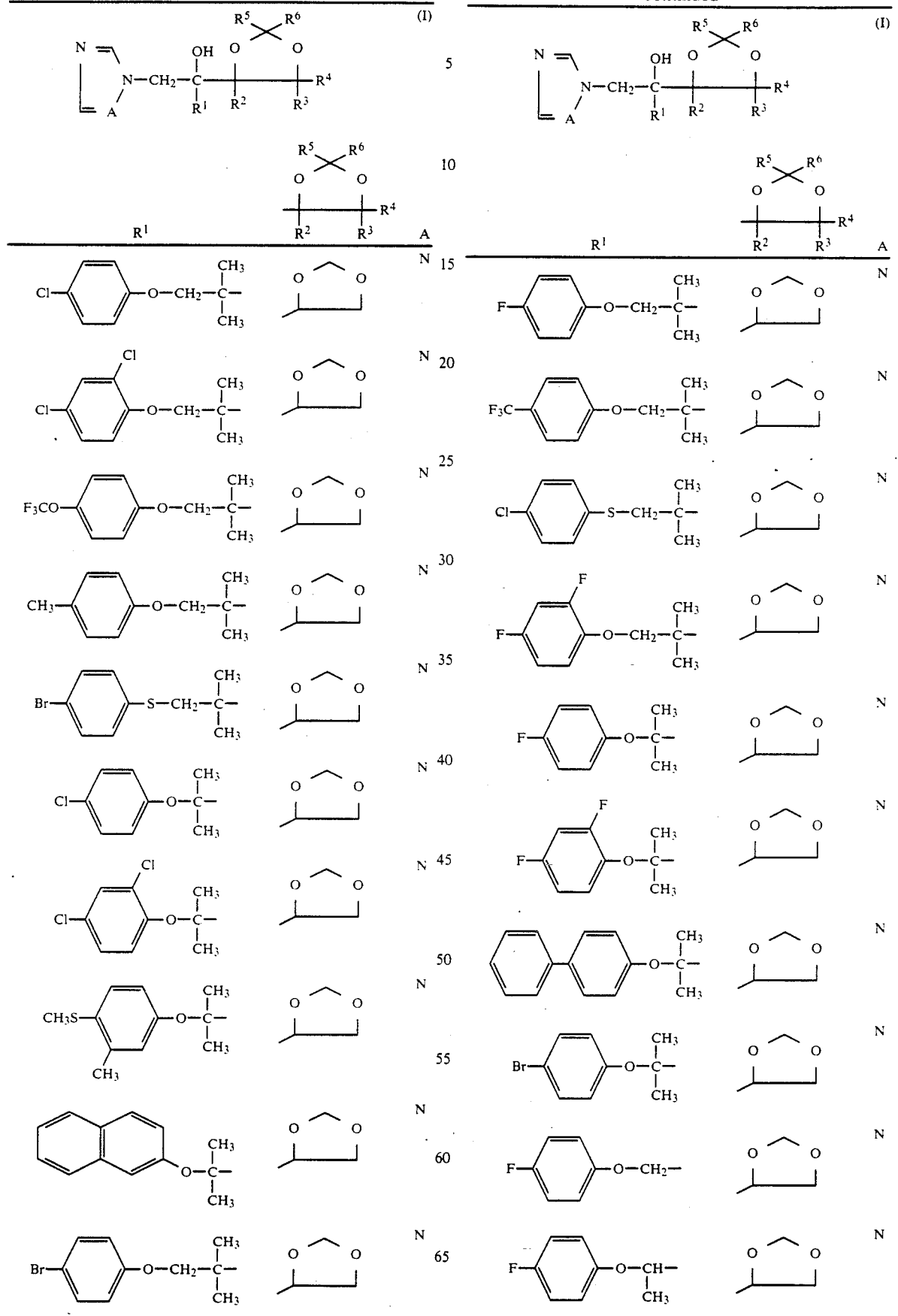

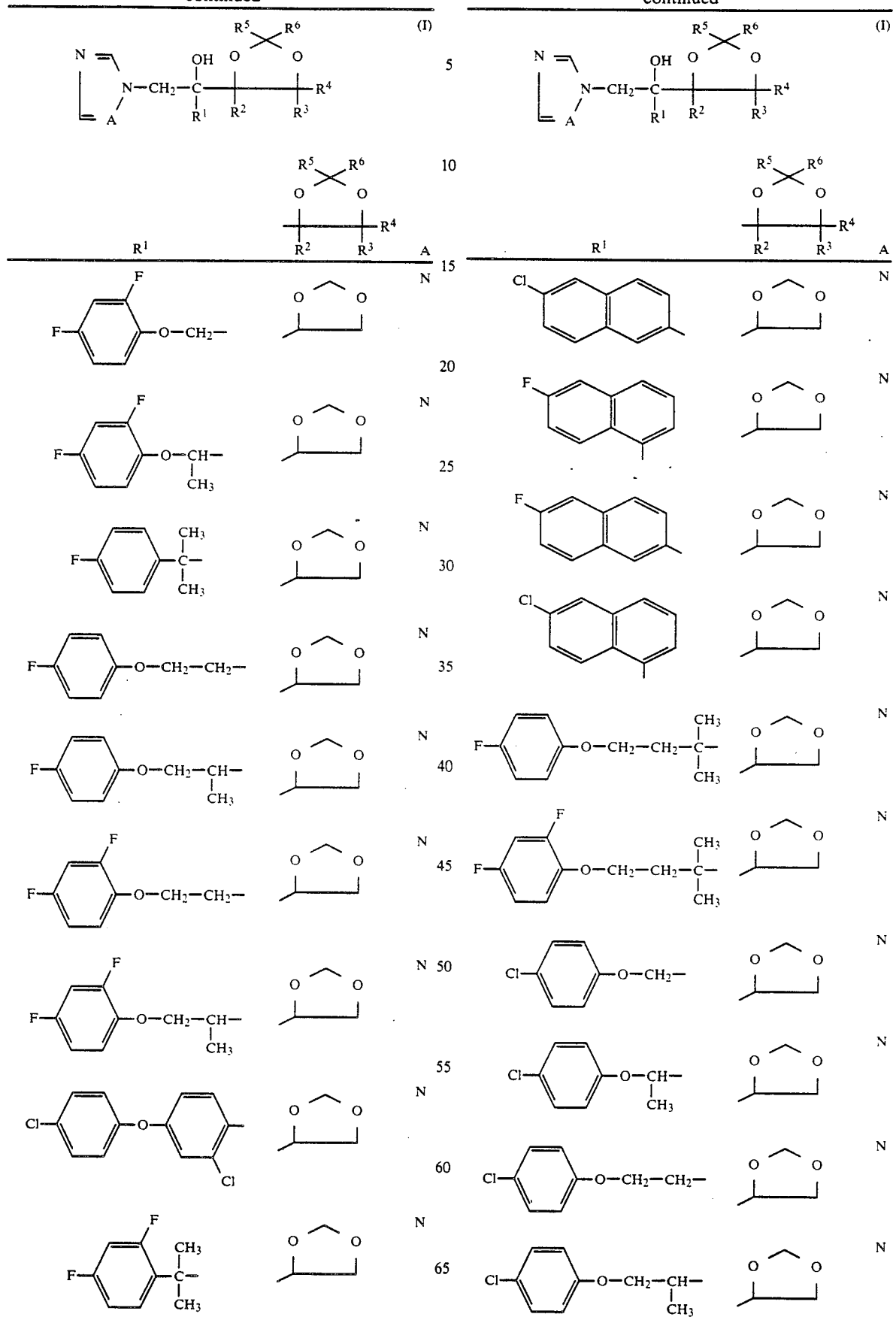

-continued
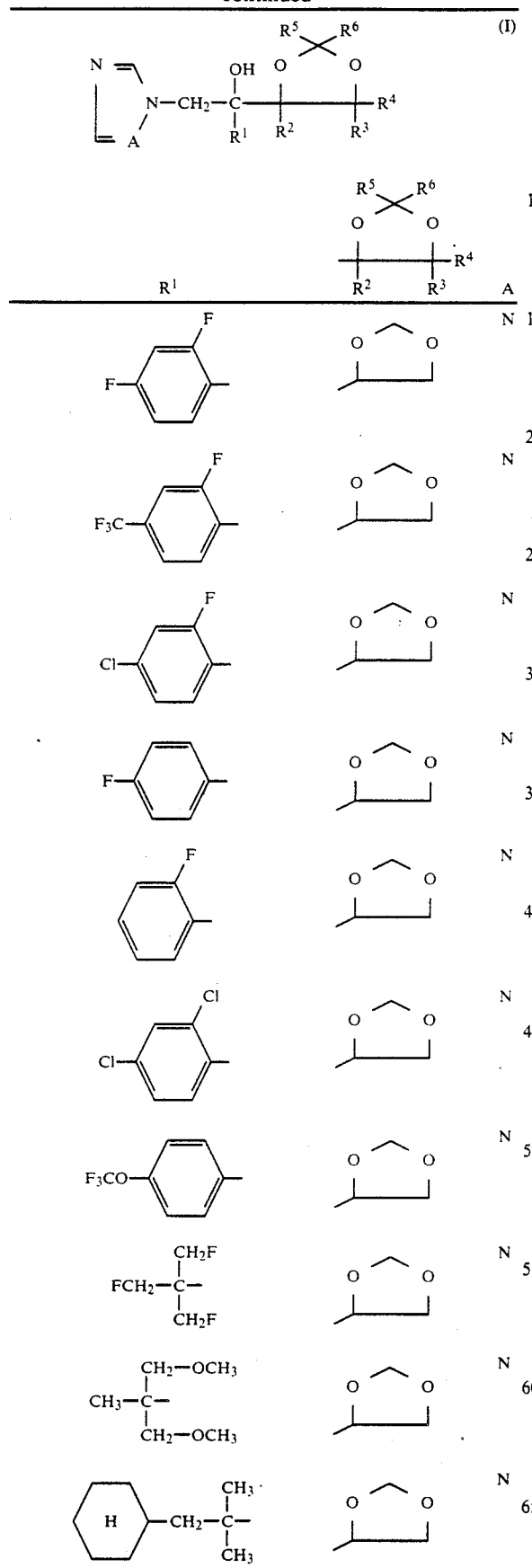
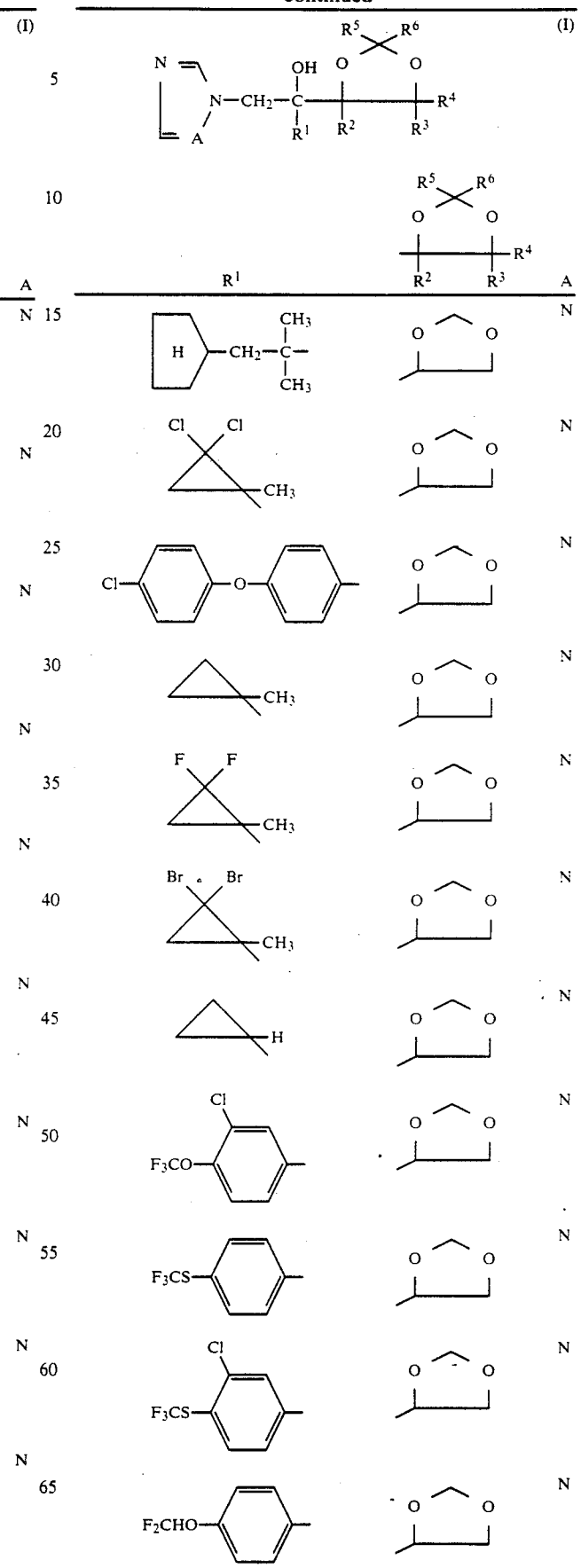

-continued
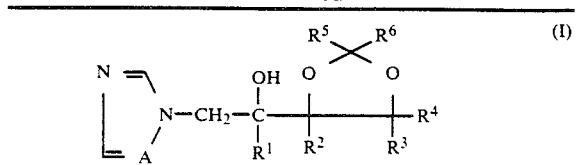
| R¹ |  | A |
|---|---|---|
| 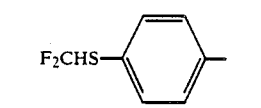 | 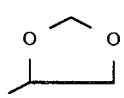 | N |
| 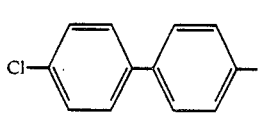 | 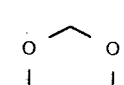 | N |
| 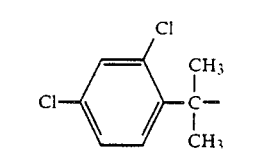 | 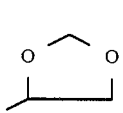 | N |
| 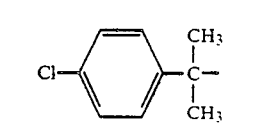 | 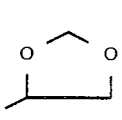 | N |
| 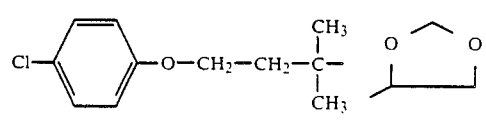 | | N |
| 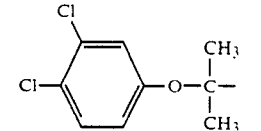 | | N |
| 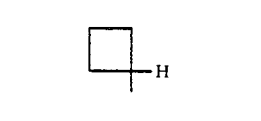 | | N |
| 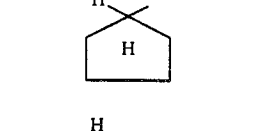 | | N |
| 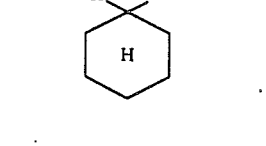 | | N |
| 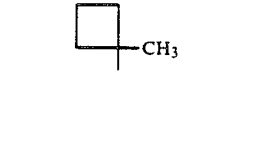 | | N |
-continued
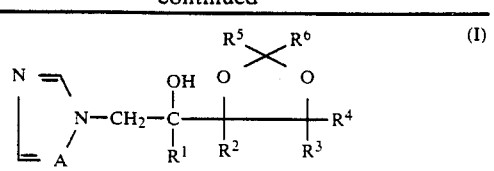
| R¹ | 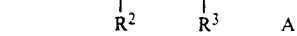 | A |
|---|---|---|
|  | | N |
|  | | N |
|  | | N |
| Cl—CH=CH—CH₂— | | N |
| (CH₃)₃C— | | N |
| (CH₃)₂CH— | | N |
| 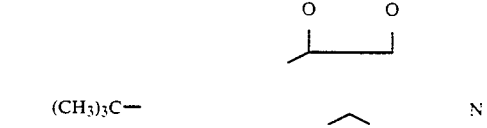 | | N |
| 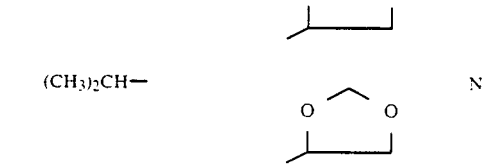 | | N |
|  | | N |
| 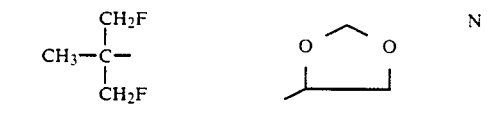 | | N |
| 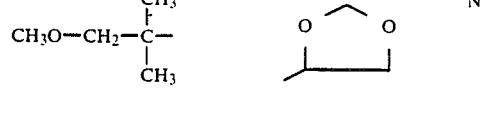 | | N |

5,081,265

-continued $$\begin{array}{c} \text{N} \\ \parallel \\ \text{CH} \\ | \\ \text{N—CH}_2\text{—C—CH—R}^4 \\ | \quad | \quad | \\ \text{A} \quad \text{R}^1 \quad \text{R}^2 \quad \text{R}^3 \end{array} \quad \text{OH} \quad \begin{array}{c} \text{R}^5 \quad \text{R}^6 \\ \diagdown / \\ \text{O} \quad \text{O} \end{array} \quad \text{(I)}$$

| R¹ | $\begin{array}{c} R^5\ R^6 \\ O\ \ O \\ \diagdown / \\ R^2\ R^3 \end{array}$ R⁴ | A |
|---|---|---|
| CH₃S—CH₂—C(CH₃)₂— | O-CH₂-O (dioxolane) | N |
| C₂H₅S—CH₂—C(CH₃)₂— | O-CH₂-O | N |
| F₃CS—C(CH₃)₂— | O-CH₂-O | N |
| CH₃—(CH₂)₂—C(CH₃)₂— | O-CH₂-O | N |
| C₂H₅—C(CH₃)₂— | O-CH₂-O | N |
| (CH₃)₂CH—C(CH₃)₂— | O-CH₂-O | N |
| CH₃—(CH₂)₃—C(CH₃)₂— | O-CH₂-O | N |
| CH₂=CH—CH₂—C(CH₃)₂— | O-CH₂-O | N |
| HC≡C—CH₂—C(CH₃)₂— | O-CH₂-O | N |
| CH₃—CH=CH—CH₂—C(CH₃)₂— | O-CH₂-O | N |
| Cl—CH=CH—CH₂—C(CH₃)₂— | O-CH₂-O | N |
| Cl—CH=C(Cl)—CH₂—C(CH₃)₂— | O-CH₂-O | N |
| Br—CH=CH—CH₂—C(CH₃)₂— | O-CH₂-O | N |
| Br—CH=C(Br)—CH₂—C(CH₃)₂— | O-CH₂-O | N |
| H₂C=CH—CH₂— | O-CH₂-O | N |
| HC≡C—CH₂— | O-CH₂-O | N |
| CH₃O—N=CH—C(CH₃)₂— | O-CH₂-O | N |
| NC—C(CH₃)₂— | O-CH₂-O | N |
| Cyclohexyl—CH₂— | O-CH₂-O | N |
| (O-CH₂-O)CH—C(CH₃)₂— (1,3-dioxolan-2-yl) | O-CH₂-O | N |
| (O-CH₂-O)CH—C(CH₃)₂— | O-CH₂-O | N |
| (S-CH₂-S)CH—C(CH₃)₂— | O-CH₂-O | N |
| (S-CH₂-CH₂-S)CH—C(CH₃)₂— | O-CH₂-O | N |

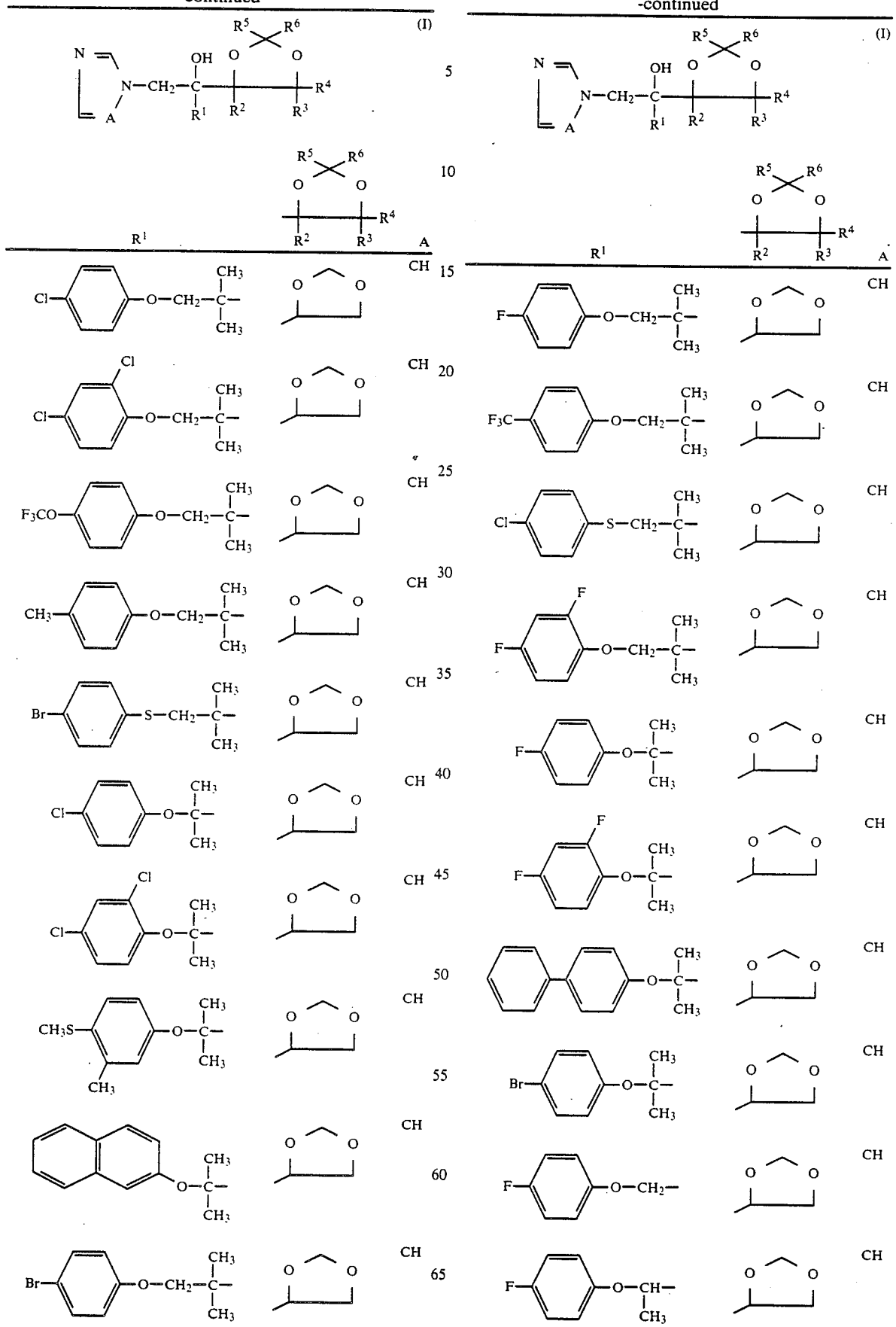

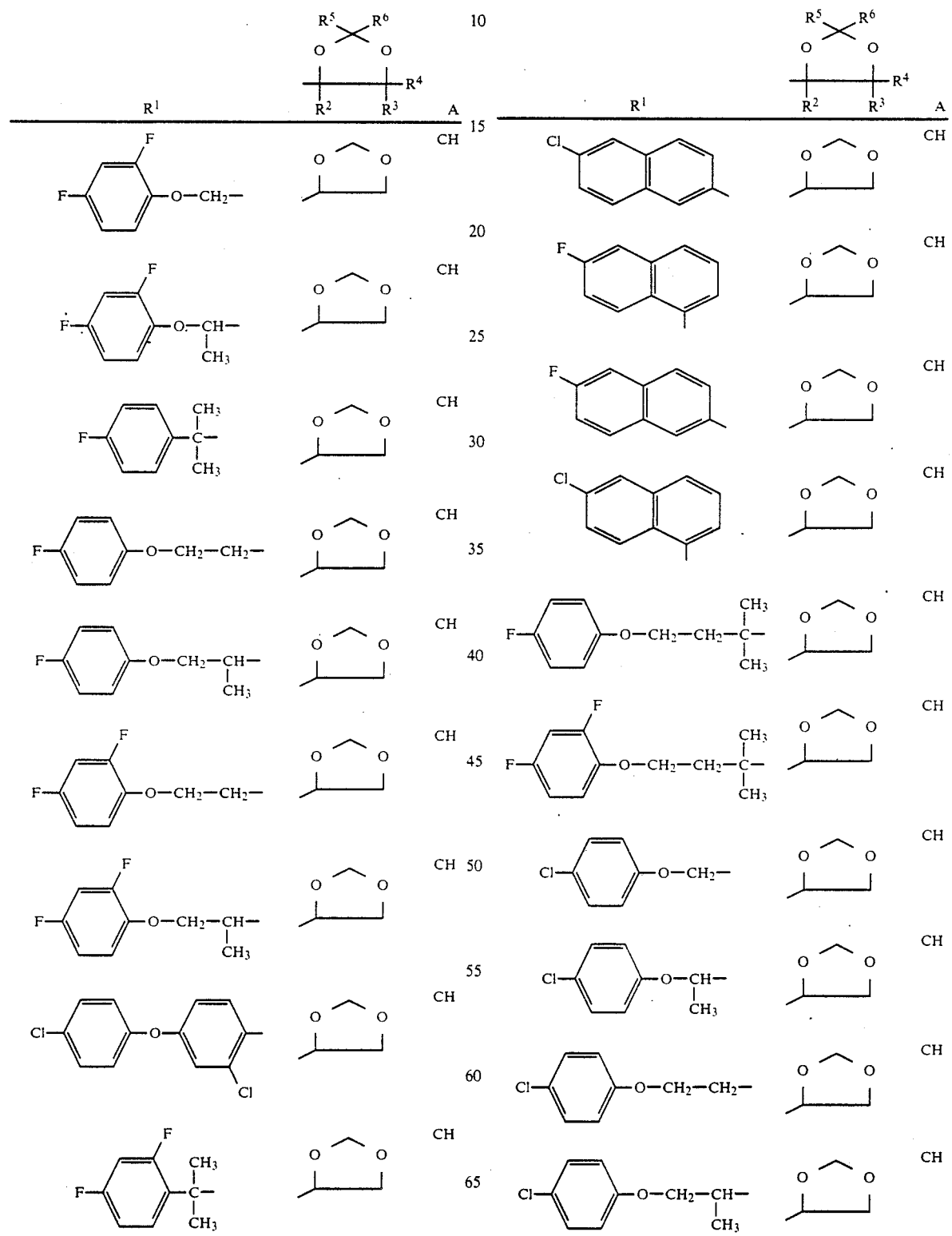

-continued $$\begin{array}{c} \phantom{N}\phantom{=}\phantom{/}R^5\phantom{ }R^6 \\ N\phantom{=}\phantom{=}\phantom{/} \\ \| \phantom{====}OH\phantom{ }O\phantom{ }O \\ \phantom{N}\phantom{=}N\text{—}CH_2\text{—}C\text{—}C\text{—}R^4 \\ \diagdown\phantom{==}| \phantom{=}| \phantom{=}| \\ \phantom{===}A\phantom{==}R^1\phantom{ }R^2\phantom{ }R^3 \end{array}\quad (I)$$

| R¹ | R² R³ (with R⁵R⁶ dioxolane, R⁴) | A |
|---|---|---|
| 2,4-difluorophenyl | –O–CH₂–O– dioxolane | CH |
| 2-F, 4-CF₃-phenyl | –O–CH₂–O– dioxolane | CH |
| 2-F, 4-Cl-phenyl | –O–CH₂–O– dioxolane | CH |
| 4-F-phenyl | –O–CH₂–O– dioxolane | CH |
| 2-F-phenyl | –O–CH₂–O– dioxolane | CH |
| 2,4-dichlorophenyl | –O–CH₂–O– dioxolane | CH |
| 4-F₃CO-phenyl | –O–CH₂–O– dioxolane | CH |
| (FCH₂)(CH₂F)(CH₂F)C– (1,3-difluoro-2-(fluoromethyl)propan-2-yl with CH₂F groups) | –O–CH₂–O– dioxolane | CH |
| CH₃–C(CH₂OCH₃)₂– | –O–CH₂–O– dioxolane | CH |
| cyclohexyl–CH₂–C(CH₃)₂(H)– | –O–CH₂–O– dioxolane | CH |
| cyclopentyl–CH₂–C(CH₃)₂(H)– | –O–CH₂–O– dioxolane | CH |
| 2,2-dichloro-1-methylcyclopropyl | –O–CH₂–O– dioxolane | CH |
| 4-(4-chlorophenoxy)phenyl | –O–CH₂–O– dioxolane | CH |
| 1-methylcyclopropyl | –O–CH₂–O– dioxolane | CH |
| 2,2-difluoro-1-methylcyclopropyl | –O–CH₂–O– dioxolane | CH |
| 2,2-dibromo-1-methylcyclopropyl | –O–CH₂–O– dioxolane | CH |
| cyclopropyl | –O–CH₂–O– dioxolane | CH |
| 2-Cl, 4-F₃CO-phenyl | –O–CH₂–O– dioxolane | CH |
| 4-F₃CS-phenyl | –O–CH₂–O– dioxolane | CH |
| 2-Cl, 4-F₃CS-phenyl | –O–CH₂–O– dioxolane | CH |
| 4-F₂CHO-phenyl | –O–CH₂–O– dioxolane | CH |

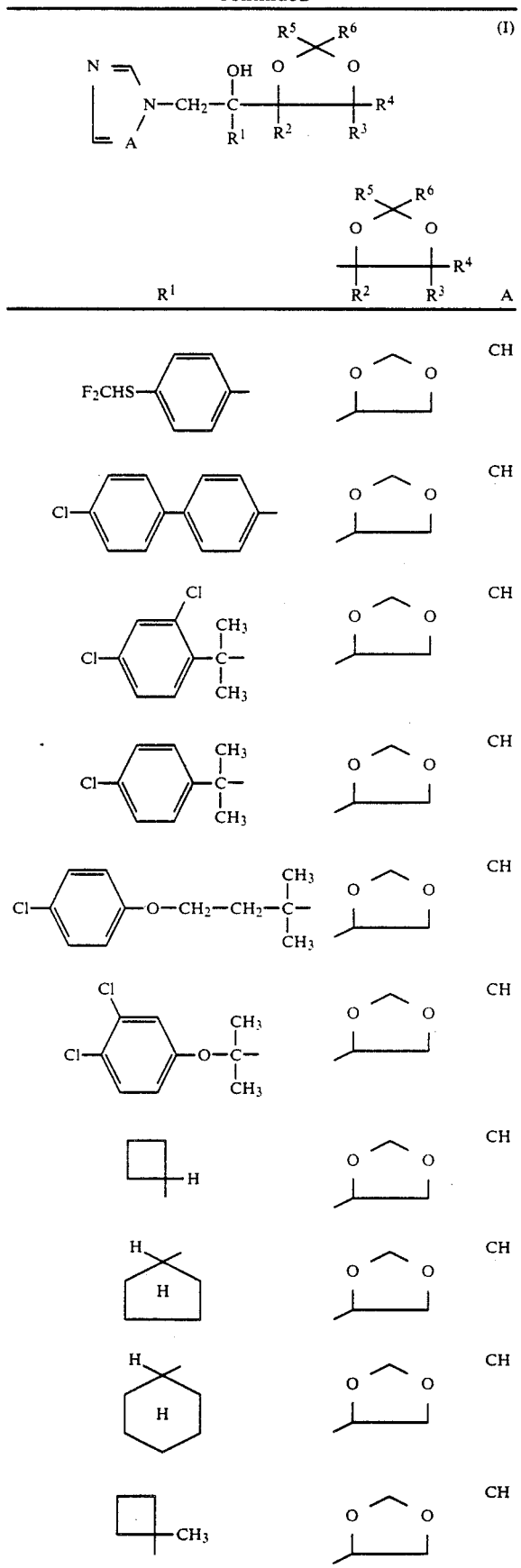
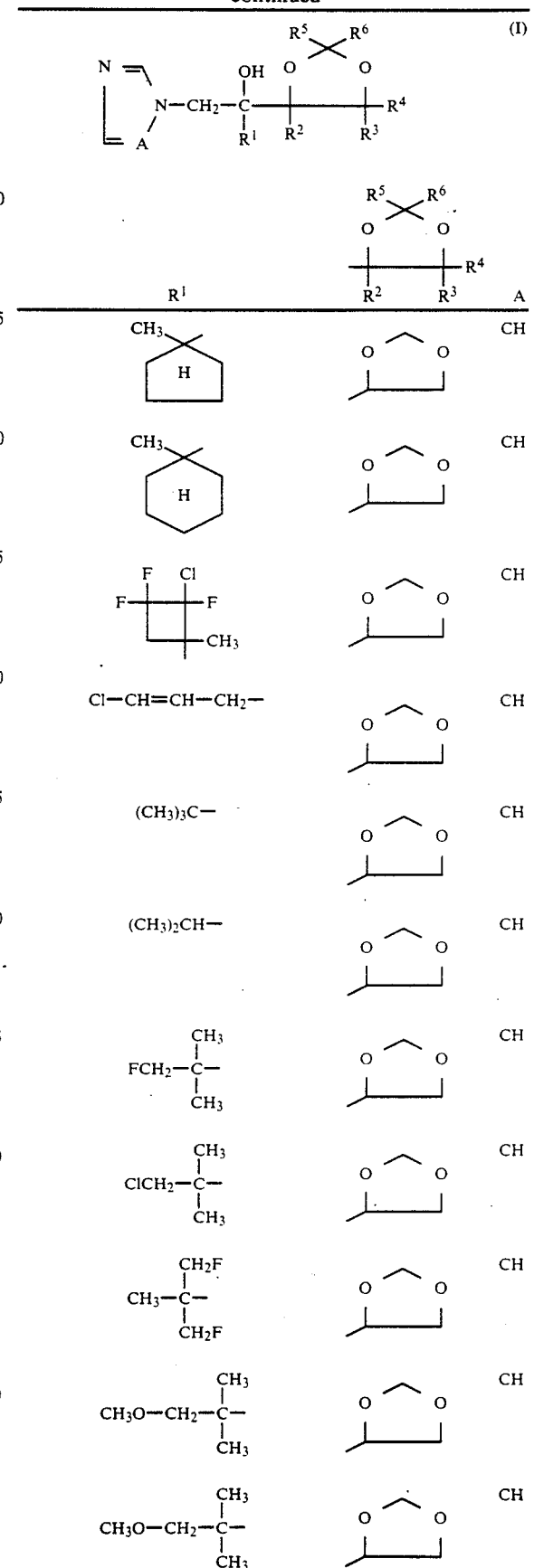

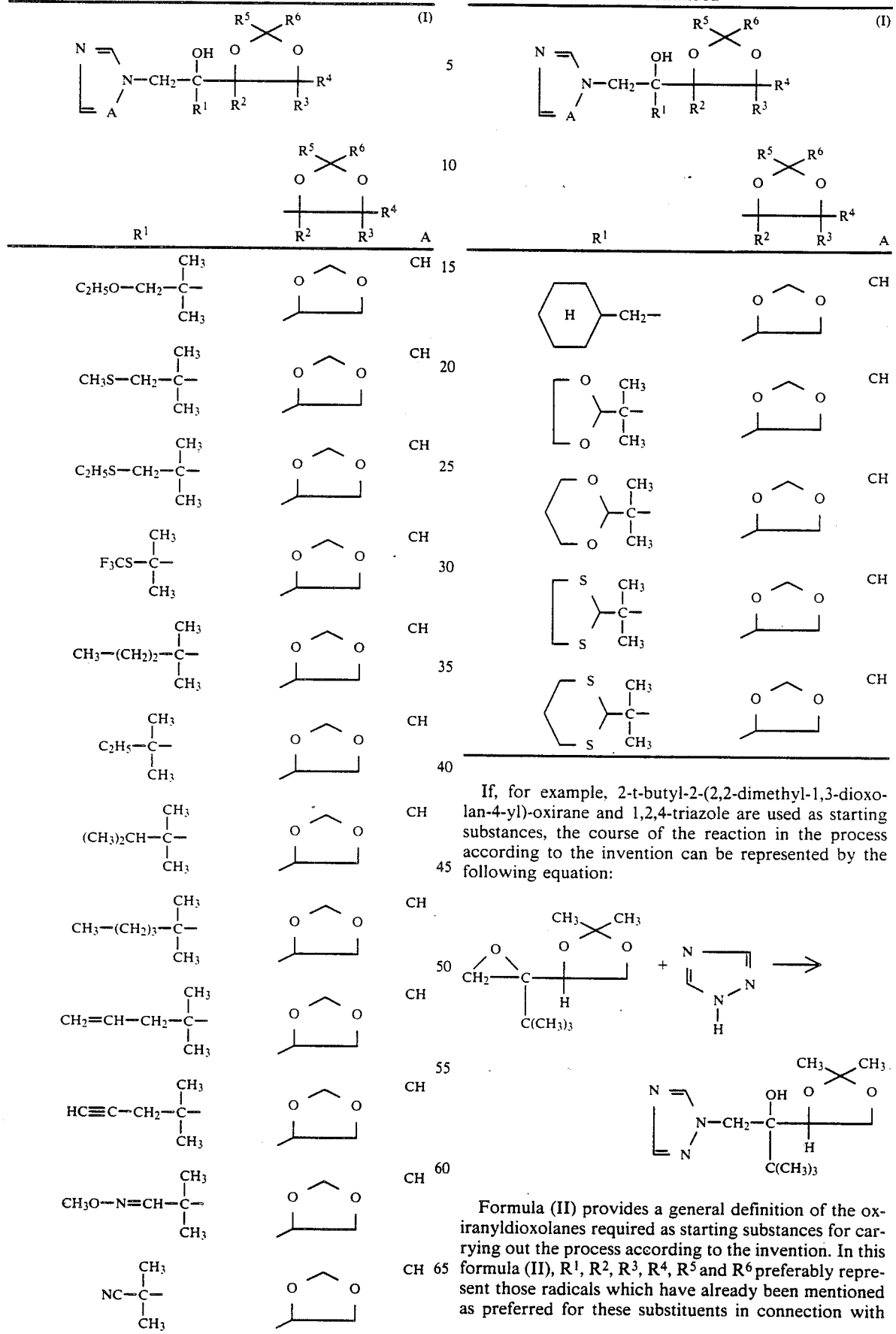

the description of the substances of the formula (I) according to the invention.

The oxiranyldioxolanes of the formula (II) are known in some cases (such as, for example, Acta chem. Scand. B 34, 41–45, [1980]; Tetrahedron 36, 3101–3105 [1980]; Tetrahedron Lett. 27, 69–70 [1986]; and JP 62/26,280).

Oxiranyldioxolanes which are not yet known and to which the invention likewise relates are those of the formula (IIa)

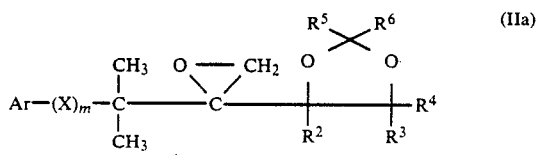

in which

Ar represents optionally substituted aryl,

X represents oxtgen, sulphur, sulphinyl or sulphonyl, or represents one of the groups —$CH_2$—; —O—$CH_2$—; —$CH_2$—O—; —O—$CH_2$—$CH_2$—; —$S(O)_n$—$CH_2$—; —$CH_2$—$S(O)_n$— or —$S(O)_n$—$CH_2$—$CH_2$—, m represents the number 0 or 1, n in each case represents the number 0, 1 or 2 and $R^2$, $R^3$, $R^4$, $R^5$ and $R^6$ have the abovementioned meanings.

Preferred oxiranyldioxolanes of the formula (IIa) are those in which

Ar represents phenyl which is unsubstituted or substituted by one or more identical or different substituents, possible substituents being: halogen, cyano, nitro, straight-chain or branched alkyl, straight-chain or branched alkoxy, straight-chain or branched alkylthio, straight-chain or branched alkylsulphinyl or straight-chain or branched alkylsulphonyl having in each case 1 to 4 carbon atoms, straight-chain or branched divalent alkanediyl having 1 to 10 carbon atoms, cycloalkyl having 3 to 7 carbon atoms, straight-chain or branched halogenoalkyl, straight-chain or branched halogenoalkoxy, straight-chain or branched halogenoalkylthio, straight-chain or branched halogenoalkylsulphinyl or straight-chain or branched halogenoalkylsulphonyl having in each case 1 to 4 carbon atoms and 1 to 9 identical or different halogen atoms, straight-chain or branched alkoxycarbonyl or straight-chain or branched alkoximinoalkyl having in each case 1 to 4 carbon atoms in the individual alkyl parts, divalent dioxyalkylene which has 1 to 6 carbon atoms and is unsubstituted or substituted by one or more identical or different halogen atoms, or phenyl or phenoxy, in each case unsubstituted or substituted by one or more identical or different halogen atoms; or represents naphthyl which is unsubstituted or substituted by one or more identical or different substituents, possible substituents being: halongen, cyano and straight-chain or branched alkyl having 1 to 4 carbon atoms;

X respesent oxygen, sulphur, sulphinyl or sulphonyl, or represents one of the the groups —$CH_2$—; —O—$CH_2$—; —$CH_2$—O—; —O—$CH_2$—$CH_2$—; —$S(O)_n$—$CH_2$—; —$CH_2$—$S(O)_n$— or —$S(O)_n$—$CH_2$—$CH_2$—, m represents the number 0 or 1, n in each case represents the number 0, 1 or 2 and $R^2$, $R^3$, $R^4$, $R^5$ and $R^6$ have the abovementioned meanings.

Particularly preferred oxiranyldioxolanes of the formula (IIa) are those in which Ar represents phenyl which is unsubstituted or substituted by one to three identical or different substituents, possible substituents being: fluorine, chlorine, bromine, cyano, nitro, methyl, ethyl, n- or i-propyl, n-, i-, s- or t-butyl, methoxy, ethoxy, n- or i-propoxy, methylthio, ethylthio, propane-1,3-diyl, butane-1,4-diyl, pentane-1,5-diyl, dimethylpropane-1,3-diyl, tetramethylpropane-1,3-diyl, dimethylbutane-1,4-diyl, tetramethylbutane-1,4-diyl, cyclopropyl, cyclobutyl, cyclopentyl, cyclohexyl, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene and dioxyethylene and phenyl and phenoxy, in each case unsubstituted or substituted by one to three identical or different substituents from the group comprising fluorine and chlorine; or represents α-naphthyl or β-naphthyl which is unsubstituted or substituted by one to three identical or different substituents, possible substituents in each case being: fluorine, chlorine, bromine, cyano, methyl, ethyl and n- or i-propyl.

X represents oxygen, sulphur, sulphinyl or sulphonyl, or represents one of the groups —$CH_2$—; —O—$CH_2$—; —$CH_2$—O—; —O—$CH_2$—$CH_2$—; —$S(O)_n$—$CH_2$—; —$CH_2$—$S(O)_n$— or —$S(O)_n$—$CH_2$—$CH_2$—, m represents the number 0 or 1, n in each case represents the number 0, 1 or 2 and $R^2$, $R^3$, $R^4$, $R^5$ and $R^6$ have the abovementioned meanings.

Especially preferred oxiranyldioxolanes of the formula (IIa) are those in which

Ar represents phenyl which is unsubstituted or substituted by one to three identical or different substituents from the group comprising fluorine, chlorine, bromine, methyl, methoxy, methylthio, trifluoromethyl, trifluoromethoxy, trifluoromethylthio, difluoromethyl, difluoromethoxy, difluoromethylthio, phenyl and phenoxy, or represents α-naphthyl or β-naphthyl, in each case unsubstituted or monosubstituted by fluorine, chlorine or methyl, X represents oxygen or sulphur, or represents one of the groups —CH₂—; —O—CH₂—; —S—CH₂—; —O—CH₂—CH₂— or —S—CH₂—CH₂—, m represents the number 0 or 1 and R², R³, R⁴, R⁵ and R⁶ have the abovementioned meanings.

These new oxiranyldioxolanes of the formula (IIa) are obtained by a process analogous to the preparation of the known oxiranyldioxolanes of the formula (II), by a procedure in which vinyl ketones of the formula (IVa)

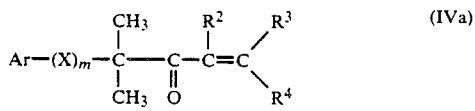

in which

Ar, X, R², R³, R⁴ and m have the meanings given in the case of formula (IIa), are epoxidized with an oxidizing agent, such as, for example, peracetic acid or m-chloroperbenzoic acid, if appropriate in the presence of a diluent, such as, for example, methylene chloride, dichlorobenzene, toluene or acetic acid, at temperatures between 10° C. and 60° C. and the oxiranyl ketones thus obtainable, of the formula (Va)

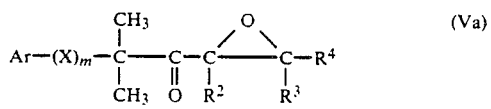

in which Ar, X, R², R³, R⁴ and m have the meanings given in the case of formula (IIa), are then reacted in a 2nd stage with aldehydes or ketones of the formula (VI)

in which R⁵ and R⁶ have the abovementioned meanings, if appropriate in the presence of a catalyst, such as, for example, tin tetrachloride, and if appropriate in the presence of a diluent, such as, for example, carbon tetrachloride, at temperatures between −80° C. and +50° C. (compare, for example, Angew. Chem. Int. Ed. Engl. 21, 449 [1982]), and the dioxolanyl ketones thus obtainable, of the formula (VIIa)

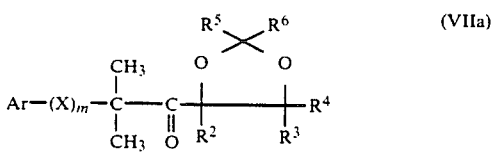

in which Ar, X, R², R³, R⁴, R⁵, R⁶ and m have the meanings given in the case of formula (IIa), are then either reacted with dimethyloxosulphonium methylide of the formula (VIII)

in a known manner in the presence of a diluent, such as, for example, dimethylsulphoxide, at temperatures between 20° C. and 80° C. (compare, for example, J. Amer. Chem. Soc. 87, 1363-1364 [1965]) or are reacted with trimethylsulphonium methylsulphate of the formula (IX)

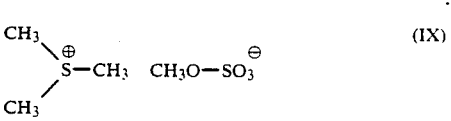

Likewise in a known manner in the presence of a diluent, such as, for example, acetonitrile, and in the presence of a base, such as, for example, sodium methylate, at temperatures between 0° C. and 60° C. (compare, for example, Heterocycles 8, 397 [1977]).

If appropriate, the oxiranyldioxolanes of the formula (II) thus obtainable can be further reacted by the process according to the invention directly from the reaction mixture without being isolated.

Vinyl ketones of the formula (IVa) are known or more obtainable by processes analogous to known processes (compare, for example, EP 6,718; DE-OS (German Published Specification) 2,922,070; Chem. Lett. 1987, 1283-1286; J. Amer. Chem. Soc. 108, 4568-4580 [1986]; J. Org. Chem. 51, 2389-2391 [1986] or An. Quim. 75, 707-711 [1979] or CA 92; 75 727a).

Oxiranyl ketones of the formula (Va) and dioxolanyl ketones of the formula (VIIa) are not yet known and the invention likewise related to them.

Dioxolanyl ketones of the formula (VII)

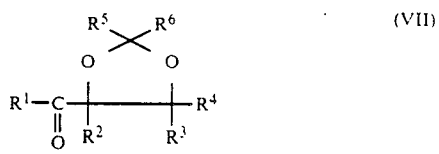

in which R¹, R², R³, R⁴, R⁵ and R⁶ have the abovementioned meanings, are known in some cases (compare, for example, J. Org. Chem. 33, 2473-2477 [1968]); Acta Chem. Scand. B 34, 41-45 [1980]; Tetrahedron 36, 3101-3105 [1980]; J. Org. Chem. 47, 3289-3296 [1982]; Tetrahedron Lett. 23, 4369-4370 [1982]; Synthesis 1986 60-61; Synth. Commun. 16, 1517-1522 [1986]; and Tetrahedron Lett. 28, 383-386 [1987]), or are obtainable by processed analogous to known processes, for example by a procedure in which dioxolanylcarbinols of the formula (X)

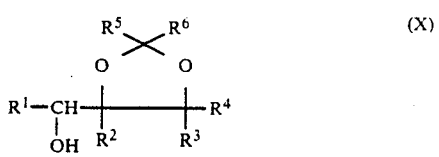

in which R¹, R², R³, R⁴, R⁵ and R⁶ have the abovementioned meanings, are oxidized with customary oxidizing agents, such as, for example, chromium trioxide, in the presence of pyridine and hydrogen chloride and if appropriate in the presence of a diluent, such as, for example, methylene chloride, at temperatures between $-20°$ C. and $+80°$ C. (compare, for example, Tetrahedron Lett. 28, 383-386 [1987]).

Dioxolanylcarbinols of the formula (X) are known or are obtainable by processes analogous to known processes (compare, for example, Tetrahedron Lett. 26, 5759-5762 [1985]).

Dioxolanyl ketones of the formula (VIIb)

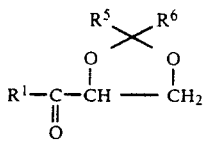

(VIIb)

in which $R^1$, $R^5$ and $R^6$ have the abovementioned meanings,
are alternatively also obtained by a process in which halogenomethyl ketones of the formula (XI)

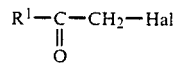

(XI)

in which
$R^1$ has the abovementioned meaning and
Hal represents halogen, in particular chlorine or bromine,
are reacted with formaldehyde, if appropriate in the presence of a diluent, such as, for example, methanol, tetrahydrofuran, or dioxane, and if appropriate in the presence of a reaction auxiliary, such as, for example, sodium methylate or sodium hydroxide solution, at temperatures between 0° C. and 120° C., either α-halogeno ketones of the formula (XII)

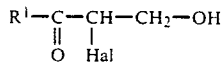

(XII)

in which $R^1$ and Hal have the abovementioned meanings,
or oxiranyl ketones of the formula (Vb)

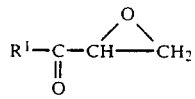

(Vb)

in which $R^1$ has the abovementioned meaning,
being formed, depending on the reaction time, reaction temperature and concentration of reaction auxiliaries, and these α-halogenoketones of the formula (XII) or the oxiranyl ketones of the formula (Vb) or a mixture of compounds of this type are reacted in a second stage with aldehydes or ketones of the formula (VI)

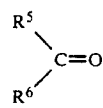

(VI)

in which $R^5$ and $R^6$ have the abovementioned meanings, if appropriate in the presence of a diluent, such as, for example, carbon tetrachloride, and if appropriate in the presence of a catalyst, such as, for example, tin tetrachloride, and if appropriate in the presence of an acid-binding agent, such as, for example, sodium methylate or sodium hydroxide, at temperatures between $-80°$ C. and $+80°$ C. (compare, for example, Angew. Chem. Int. Ed. Engl. 21, 449 [1982]).

Aldehydes and ketones of the formula (VI) are generally known compounds of organic chemistry.

Halogenomethyl ketones of the formula (XI) are likewise generally known compounds of organic chemistry, or are obtainable by processes analogous to generally known processes.

Oxiranyl ketones of the formula (Vb) are known in some cases (compare, for example, Can. J. Chem. 62, 2429-2434 [1984]; Tetrahedron 40, 1381-1390 [1984]; Chem. Lett. 1982, 1601-1604; J. Org. Chem. 45, 3407-3413 [1980]; J. Org. Chem. 43, 1323-1327 [1978]; Chem. Ber. 108, 2391-2396 [1975]; and J. Org. Chem. 39, 388-393 [1974]).

α-Hlogenoketones of the formula (XII) are likewise known in some cases (compare, for example, Tetrahedron Lett. 28, 383-386 [1987]; Synth. Commun. 16, 1517-1522 [1986]; Synthesis 1986, 60-61; Tetrahedron Lett. 23, 4369-4370 [1982]; J. Org. Chem. 47, 3289-3296 [1982]; Tetrahedron 36, 3101-3105 [1980]; Acta Chem. Scand B 34, 41-45 [1980]; and J. Org. Chem. 33, 2473-2477 [1968]).

α-Halogenoketones which are not yet known are those of the formula (XIIa)

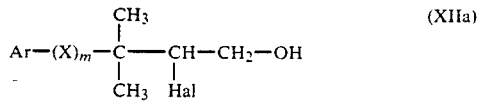

(XIIa)

in which
Hal represents halogen, in particular chlorine or bromine, and
Ar, X and m have the abovementioned meanings.

They are obtained by a process analogous to the abovementioned general process, by a procedure in which halogenomethyl ketones of the formula (XIa)

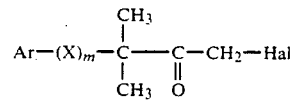

(XIa)

in which Ar, X, Hal and m have the abovementioned meanings,
are reacted with formaldehyde, if appropriate in the presence of a diluent, such as, for example, methanol, ethanol, tetrahydrofuran or dioxane, and if appropriate in the presence of a reaction auxiliary, such as, for example, sodium methylate, at temperatures between 0° C. and 60° C.

Halogenomethyl ketones of the formula (XIa) are known or are obtainable by processes analogous to known processes (compare, for example, DE-OS (German Published Specification) 2,632,603; DE-OS (German Published Specification) 3,021,516; and EP 54,865).

Dioxolanyl ketones of the formula (VIIc)

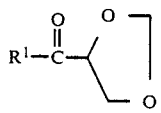 (VIIc)

in which $R^1$ has the abovementioned meaning,
are alternatively also obtained by a process in which halogenomethyl ketones of the formula (XI)

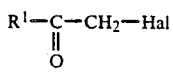 (XI)

in which
$R^1$ has the abovementioned meaning and
Hal represents halogen, in particular chlorine or bromine,
are reacted with at least two equivalents of formaldehyde, if appropriate in the presence of a diluent, such as, for example, methanol or tetrahydrofuran, and if appropriate in the presence of an acid-binding agent, such as, for example, sodium methylate or sodium hydroxide, at temperatures between 20° C. and 80° C., α-halogenoketones of the formula (XII) intermediately occurring not being isolated.

Formula (III) provides a general definition of the azoles furthermore required as starting substances for carrying out the process according to the invention. In this formula (III), A preferably represents those radicals which have already been mentioned as preferred for this substituent in connection with the description of the substances of the formula (I) according to the invention.

Azoles of the formula (III) are generally known compounds or organic chemistry.

Possible diluents for carrying out the process according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or prpionitrile, amides, such as dimethylformamide, dimethylacetamide, N-methylformanilide, N-methylpyrrolidone or hexamethylphosphoric acid triamide, esters, such as ethyl acetate, sulphoxides, such as dimethylsulphoxide, or alcohols, such as methanol, ethanol, propanol, butanol, methoxyethanol or ethyoxyethanol.

The process according to the invention is preferably carried out in the presence of a suitable reaction auxiliary. Possible auxiliaries are all the inorganic and organic bases which can usually be employed. Bases which are preferably used are alkali metal hydrides, hydroxides, amides, alcoholates, carbonates or bicarbonates, such as, for example, sodium hydride, sodium amide, sodium hydroxide, sodium methylate, sodium ethylate, potassium t-butylate, sodium carbonate or sodium bicarbonate, or also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

It may moreover be of advantage, if appropriate, to employ catalytic amounts of any customary agent which forms free radicals, such as, for example, α,α'-azodiisobutyronitrile (AIBN), as a reaction auxiliary.

The reaction temperatures can be varied within a substantial range in carrying out the process according to the invention. The reaction is in general carried out at temperatures between 0° C. and 200° C., preferably at temperatures between 60° C. and 150° C.

The process according to the invention is in general carried out under normal pressure. However, it is also possible to carry out the reaction under increased or reduced pressure.

For carrying out the process according to the invention, in general 1.0 to 5.0 mols, preferably 1.0 to 1.2 mols, of azole of the formula (III) and if appropriate 1.0 to 5.0 mols, preferably 1.0 to 2.0 mols, of reaction auxiliary are employed per mol of oxiranyldioxolane of the formula (II).

The reaction is carried out and the reaction products are worked up and isolated by generally customary methods (compare also the preparation examples).

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

The metal salt complexes of compounds of the formule (I) can be obtained in a simple manner by customary processes, thus, for example, by dissolving the metal salt in alcohol, for example ethanol, and adding the solution to the compound of the formula (I). Metal salt complexes can be isolated in a known manner, for example by filtration, and if appropriate purified by recrystallization.

The substituted dioxolanes of the formula (I) can moreover be used as interesting intermediate products for the preparation of other active compounds.

For example, they can be reacted on the hydroxyl group by alkylation or acylation with customary alkyl halides or alkyl sulphates or with acyl halides or carbamoyl halides, to give the corresponding ethers, esters, carbonates or carbamates, which likewise have a good activity as fungicides.

The active compounds according to the invention exhibit a potent action against undesirable microorganisms. The active compounds are preferably suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating cereals diseases, such as, for example, against the powdery mildew of cereal causative organism (*Erysiphe graminis*) or against the cereal brown rust on wheat causative organism (*Puccinia recondita*) or against the brown glume of wheat causative organism (*Leptosphaeria nodorum*) or against the net spot disease of barley causative organism (*Pyrenophora teres*) or against the brown spot disease on barley and wheat causative organism (*Cochliobolus sativus*), or for combating rice diseases, such as, for example, against the rice spot disease causative organism (*Pyricularia oryzae*), or for combating diseases in fruit and vegetable growing, such as, for example, against the bean grey mould causative organism (*Botrytis cinerea*) or against the apple scab causative organism (*Venturia inaequalis*).

The active compounds according to the invention moreover exhibit a good fungicidal in vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compounds of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

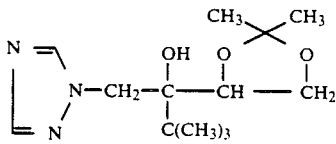

12.4 g (0.062 mol) of 2-t-butyl-2-(2,2-dimethyl-1,3-dioxolan-4-yl)-oxirane, 5.1 g (0.074 mol) of triazole and 3 g (0.074 mol) of sodium hydroxide are dissolved in 60 ml of dimethylformamide and the mixture is stirred at 100° C. for 10 hours. For working up, the cooled reaction mixture is introduced into water and extracted with ethyl acetate, the organic phase is washed with water, dried over sodium sulphate and concentrated in vacuo and the residue is purified by column chromatography on silica gel (mobile phase: ethyl acetate/cyclohexane 3:1). 4.4 g (26% of theory) of 2,2-dimethyl-1-(2,2-dimethyl-1,3-dioxolan-4-yl)-1-(1,2,4-triazol-1-yl-methyl)-propan-1-ol are obtained as an oil of refractive index $n_D^{20}$ 1.4890;

$^1$H-NMR (CDCl$_3$/tetramethylsilane): $\delta$ = 1.0 (s, 9H); 1.30 (s, 3H); 1.31 (s, 3H) ppm.

PREPARATION OF THE STARTING COMPOUNDS

EXAMPLE II-1

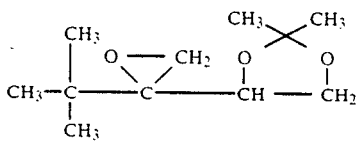

9 g (0.08 mol) of potassium t-butylate are added to 17.6 g (0.08 mol) of trimethyloxosulphonium iodide in 17.5 g (0.22 mol) of dimethylsulphoxide at room temperature, the mixture is stirred at room temperature for 6 hours, 13 g (0.0698 mol) of 4-(2,2-dimethylpropanoyl)-2,2-dimethyl-1,3-dioxolane are then added dropwise, while stirring, and the mixture is stirred at room temperature for a further 8 hours and then under reflux for 1 hour. For working up, the cooled reaction mixture is introduced into water and extracted with methylene chloride and the organic phase is washed with water, dried over sodium sulphate and concentrated in vacuo.

12.4 g (89% of theory) of 2-t-butyl-2-(2,2-dimethyl-1,3-dioxolan-4-yl)-oxirane of refractive index $n_D^{20}$ 1.4519 are obtained.

EXAMPLE VII-1

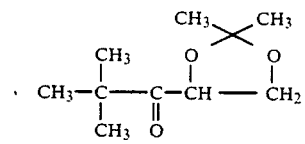

5.2 g (0.02 mol) of tin tetrachloride are added dropwise to 5.8 g (0.1 mol) of acetone and 12.8 g of 2-(2,2-dimethylpropanoyl)-oxirane in 50 ml of carbon tetrachloride at $-35°$ C., while stirring, and when the addition has ended the reaction mixture is stirred at $-35°$ C. for a further 3 hours, allowed to come to 0° C. and introduced into 50 ml of water, while cooling with ice. The organic phase is separated off, washed with water, dried over sodium sulphate and concentrated in vacuo and the residue is distilled.

8.6 g (46% of theory) of 4-(2,2-dimethylpropanoyl)-2,2-dimethyl-1,3-dioxolane are obtained MS (m/e = 186, 171, 141, 129, 101, 57).

EXAMPLE V-1

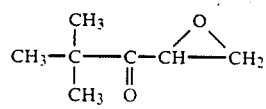

44.4 g (0.5 mol) of a 45 per cent strength sodium hydroxide solution are added dropwise to 67.3 g (0.5 mol) of t-butyl chloromethyl ketone (compare, for example, Bull. Soc. Chim. Fr. 1970, 3641-3646) and 42.9 g (0.5 mol of 35) per cent strength aqueous formaldehyde solution in 400 ml of methanol at room temperature, while stirring, and when the addition has ended the mixture is heated at the reflux temperature for 2 hours, the pH value being kept constant at pH 14 by addition of further sodium hydroxide solution. For working up, the mixture is neutralized with aqueous hydrochloric acid, the methanol is distilled off in vacuo, the residue is extracted with methylene chloride and the extract is dried over sodium sulphate and distilled.

31.5 g (49% of theory) of 2-(2,2-dimethylpropanoyl)-oxirane of boiling point 72°-75° C. under 20 mbar are obtained.

$^1$H-NMR (CDCl$_3$/tetramethylsilane): $\delta$ = 1.27 (s, 9H); 3.86 (m, 1H) ppm.

The following substituted dioxolanes of the general formula (I) are obtained in a corresponding manner and in accordance with the general instructions on the preparation:

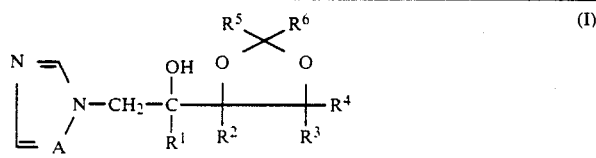
(I)

| Example No. | R¹ | (structure with R², R³, R⁴, R⁵, R⁶) | A | Physical properties |
|---|---|---|---|---|
| 2 | (CH₃)₃C— | ⟨O-CH(−)-CH₂-O⟩ | N | $^1$H-NMR*): 1.02; 7.98; 8.15 |
| 3 | 4-Cl-C₆H₄-CH₂-C(CH₃)₂— | ⟨O-CH(−)-CH₂-O⟩ | N | mp 65° C. |
| 4 | 4-Cl-C₆H₄— | ⟨O-CH(−)-CH₂-O⟩ | N | mp 175° C. |
| 5 | 3-Cl-4-F₃CO-C₆H₃-CH₂-C(CH₃)₂— | ⟨O-CH(−)-CH₂-O⟩ | N | $^1$H-NMR*): 8.02; 8.21 |
| 6 | 2,4-Cl₂-C₆H₃-CH₂-C(CH₃)₂— | ⟨O-CH(−)-CH₂-O⟩ | N | $^1$H-NMR*): 4.77 |
| 7 | 4-Br-C₆H₄-CH₂-C(CH₃)₂— | ⟨O-CH(−)-CH₂-O⟩ | N | $^1$H-NMR*): 0.89; 0.895 |
| 8 | C₆H₁₁-CH₂-C(CH₃)₂— | ⟨O-CH(−)-CH₂-O⟩ | N | $^1$H-NMR*): 4.72; 4.91; 1.00 |

(Diastereomer A)

| 9 | C₆H₁₁-CH₂-C(CH₃)₂— | ⟨O-CH(−)-CH₂-O⟩ | N | $^1$H-NMR*): 0.9 |

(Diastereomer B)

| 10 | 2-Cl-C₆H₄-CH₂-C(CH₃)₂— | ⟨O-CH(−)-CH₂-O⟩ | N | $^1$H-NMR*): 0.95, 0.99 |

-continued $$\underset{A}{\underset{\diagdown}{\overset{N=\diagdown}{\underset{\diagup}{N}}}}-CH_2-\underset{R^1}{\overset{OH}{\underset{|}{C}}}-\underset{R^2}{\overset{\overset{R^5\diagdown\diagup R^6}{\overset{|}{C}}}{\underset{|}{\underset{|}{\overset{O}{\underset{|}{\overset{|}{C}}}}}}}-R^4 \qquad (I)$$

| Example No. | R¹ | $\begin{array}{c} R^5 \diagdown R^6 \\ O \underset{|}{\overset{|}{C}} O \\ \underset{R^2}{\overset{|}{\underset{|}{C}}}\underset{R^3}{\overset{|}{\underset{|}{C}}}R^4 \end{array}$ | A | Physical properties |
|---|---|---|---|---|
| 11 | C₆H₅—CH₂—C(CH₃)₂— | isopropylidenedioxy-CH₂— | N | $n_D^{20}$ 1.5346 |
| 12 | 4-CH₃—C₆H₄—CH₂—C(CH₃)₂— | isopropylidenedioxy-CH₂— | N | mp 102–104° C. |
| 13 | 4-Cl—C₆H₄—O—C(CH₃)₂— | isopropylidenedioxy-CH₂— | N | ¹H-NMR*): 1.26; 1.33 |

*)The ¹H-NMR spectra were recorded in deuterochloroform (CDCl₃) using tetramethylsilane (TMS) as the internal standard. The chemical shift is stated as the δ value in ppm.

USE EXAMPLES

The compounds shown below were employed as comparison substances in the use examples which follow:

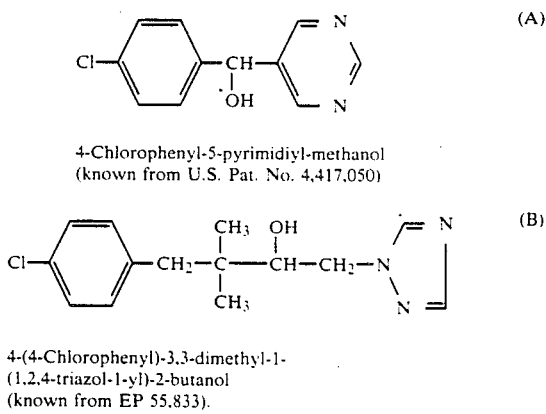

4-Chlorophenyl-5-pyrimidinyl-methanol
(known from U.S. Pat. No. 4,417,050)         (A)

4-(4-Chlorophenyl)-3,3-dimethyl-1-
(1,2,4-triazol-1-yl)-2-butanol
(known from EP 55,833).         (B)

EXAMPLE A

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

Compared with compound B, the compounds of Preparation Examples 3 and 4 at a concentration of, for example, 10 ppm exhibit a very high degree of action. Compound B is virtually inactive.

EXAMPLE B

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

Compared with compound A, the compound of Preparation Example 3 at a concentration of, for example, 0.025% strength active compound formulation exhibits a very high degree of action. Compound A is virtually inactive.

EXAMPLE C

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

Compared with compound (B), the compounds of Preparation Examples (3), (5), (10) and (12) at a concentration of, for example, 0.0025% by weight exhibit a degree of action which is 50 to 75% higher.

EXAMPLE D

*Cochliobolus sativus* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

Compared with compound (B), the compounds of Preparation Examples (3), (5), (10) and (12) at a concentration of, for example, 0.025% by weight exhibit a degree of action which is 63 to 75% higher.

EXAMPLE E

*Pyrenophora teres* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

Compared with compound (B), the compounds of Preparation Examples (3), (5), (10) and (12) at a concentration of, for example, 0.025% by weight exhibit a degree of action which is 46 to 55% higher.

It is understood that the specification and examples are illustrative but not limitative of the present invention and that other embodiments within the spirit and scope of the invention will suggest themselves to those skilled in the art.

We claim:

1. An oxiranyldioxolane of the formula $$Ar-(X)_m-\underset{\underset{CH_3}{|}}{\overset{\underset{CH_3}{|}}{C}}-\underset{\underset{}{|}}{\overset{\underset{O-CH_2}{\diagdown\diagup}}{C}}-\underset{R^2}{\overset{R^5}{|}}\underset{R^3}{\overset{R^6}{|}}-H \quad (IIa)$$

in which
Ar represents phenyl optionally substituted by 1 to 3 identical or different substituents selected from the group consisting of fluorine, chlorine, bromine, methyl and trifluoromethoxy,
X represents oxygen or a $CH_2$ group,
m represents the number 0 or 1, and
$R^2$, $R^3$, $R^5$ and $R^6$, each independently, represents hydrogen or methyl.

* * * * *